United States Patent [19]
Pinto

[11] Patent Number: 4,778,662
[45] Date of Patent: Oct. 18, 1988

[54] SYNTHESIS PROCESS AND REACTOR

[75] Inventor: Alwyn Pinto, Middlesbrough, England

[73] Assignee: Imperial Chemical Industries PLC, London, England

[21] Appl. No.: 61,035

[22] Filed: Jun. 12, 1987

Related U.S. Application Data

[63] Continuation of Ser. No. 746,019, Jun. 19, 1985, abandoned, which is a continuation of Ser. No. 442,978, Nov. 19, 1982, abandoned.

[30] Foreign Application Priority Data

Nov. 19, 1981 [GB] United Kingdom ................ 8134920

[51] Int. Cl.$^4$ .............................................. B01J 8/02
[52] U.S. Cl. .................................. 422/148; 422/203; 422/211
[58] Field of Search ............... 422/158, 118, 200, 201, 422/203, 208, 197, 148, 211

[56] References Cited

U.S. PATENT DOCUMENTS

| | | | |
|---|---|---|---|
| 1,909,378 | 5/1933 | Richardson | 422/148 X |
| 1,927,286 | 9/1933 | Jaeger et al. | 422/208 |
| 1,932,247 | 10/1933 | Kniskern | 422/148 X |
| 1,962,301 | 6/1934 | Etienne et al. | 422/208 |
| 2,052,326 | 8/1936 | Uhde | 422/148 X |
| 2,512,586 | 6/1950 | Shengel | 422/148 X |
| 2,538,738 | 1/1951 | Stengel | 422/148 |
| 2,744,813 | 5/1956 | Paul | 422/208 X |
| 2,852,350 | 9/1958 | Kolbel et al. | 422/201 |
| 3,442,626 | 5/1969 | Browne | 422/148 |
| 3,458,289 | 7/1969 | King et al. | |
| 3,466,152 | 9/1969 | Yamamoto et al. | 422/148 |
| 3,475,136 | 10/1969 | Eschenbrenner et al. | |
| 4,148,866 | 4/1979 | Becker | |
| 4,311,671 | 1/1982 | Notman | |
| 4,321,234 | 3/1982 | Ohsaki et al. | |
| 4,359,448 | 11/1982 | Schuurman et al. | 422/201 X |

FOREIGN PATENT DOCUMENTS

| | | | |
|---|---|---|---|
| 665748 | 7/1965 | Belgium | |
| 993 | 3/1979 | European Pat. Off. | |
| 626501 | 9/1927 | France | 422/148 |
| 301586 | 12/1963 | Netherlands | |
| 55446 | 6/1968 | Poland | 422/148 |
| 221229 | 9/1924 | United Kingdom | |

OTHER PUBLICATIONS

"Ammonia", Slack et al., Marcel Delcker, Inc, 1977, pp. 321-322.
Slack et al., Chem. Eng. Progress 1953, 49(8), 393-40.
European Search Report EP 82 30 5701.

Primary Examiner—Michael S. Marcus
Attorney, Agent, or Firm—Cushman, Darby & Cushman

[57] ABSTRACT

A reactor suitable for synthesis of ammonia or methanol comprises a catalyst bed 36 equipped with heat exchange tubes 32 supported by means 28-31 or 40, 42 providing catalyst fillable space between the tubes over substantially their whole length. Preferably catalyst particles between the tubes and in an uncooled bed 36 downstream thereof constitute a single body of catalyst. The reactor is especially suitable for synthesis at low pressures such that the heat transfer area provided by the tubes is relatively low.

6 Claims, 2 Drawing Sheets

SYNTHESIS PROCESS AND REACTOR

This is a continuation of application Ser. No. 746,019, filed June 19, 1985, now abandoned, which is a continuation of application Ser. No. 442,978, filed 11/19/82, now abandoned.

This invention relates to a synthesis process, especially a heterogeneous exothermic catalytic process such as for making ammonia or methanol, and a reactor for carrying it out.

In such processes the reaction temperature must be controlled in order to obtain favourable chemical equilibrium and to avoid damaging the catalyst. This has been done by (a) disposing indirect heat exchange surfaces in contact with the catalyst or (b) by subdividing the catalyst into a number of beds and cooling the reactants between the beds by indirect heat exchange or by injection of cooler gas ("quench gas"). When indirect heat exchange has been used, the fluid on the cold side of the heat exchanger has usually been reactant gas at a temperature below the catalyst inlet temperature, so that the heat exchange preheats that gas. It has been proposed to use other fluids such as boiling water but these have had limited use in ammonia synthesis, though more in methanol synthesis.

Although in principle either method could be used at any synthesis pressure, for ammonia synthesis method (a) has been used mainly at pressures over about 250 bar abs., which are now regarded as "high": see Slack et al., Chemical Engineering Progress 1953, 49, (8), 393–40. It is scarcely if at all been used in any ammonia plant designed since about 1965 or having an output over about 600 metric tons per day. Instead the multi-bed reactor, especially with quench cooling between beds, has been preferred and has afforded substantial advantages in simplicity of construction and of charging and discharging the catalyst. For examples of quench reactors reference is made to U.S. Pat. Nos. 3,458,289 and 3,475,136. Their operating pressure is typically 150 or 220 bar abs. and will be referred to as "medium pressure".

Since 1976 attempts have been made to develop an ammonia synthesis process at a still lower pressure, for example as described in U.S. Pat. No. 4,148,866 (specifically 33 at.), and European published applications No. 993 (specifically 47 bar abs.) and 26057 (105 bar abs.). Whereas EP No. 993 does not disclose any particular synthesis reactor, U.S. Pat. No. 4,148,866 and EP No. 26057 clearly teach use of a multi-bed quench reactor, similar to what has been used at higher pressures. A tube-cooled synthesis has recently been described in UK No. 2046618.

We have now found that for such low pressure processes the quench reactor is subject to the serious defect that its volume must be very large, and that it is possible to design a much smaller reactor capable of no less ammonia output. Our reactor is based on a new way of providing indirect heat exchange surfaces within the catalyst bed, following an analysis of the requirements of these low pressure processes.

According to the invention a reactor comprises a vertically oriented bed for particulate catalyst, a plurality of vertically oriented heat exchange tubes within the bed and means to supply reactant gas to the bottom of such tubes and to feed it from the upper end of such tubes downwardly through the bed, characterised in that the tubes are supported by means providing catalyst-fillable space between them over substantially their whole length.

Thus the reactor differs from known reactors, in which the tubes are supported in a tube-plate. As a result of the catalyst-filled space between the tubes, catalyst particles can pass between them during charging and discharging catalyst. Further, the catalyst particles between the tubes and those beneath it constitute a continuous body of catalyst, so that an uncooled bed can follow the cooled bed without occupying so much reactor volume as would be required if separated beds were present.

The reactor preferably includes such a bed having no heat exchange surface or less than the tube-cooled bed. The effect of such a bed is to increase the quantity of the synthesis product by a small but useful amount, typically 1–5% in ammonia synthesis at 30–120 bar abs. pressure or 0.1 to 0.5% in methanol synthesis at such pressures. The resulting higher temperature of the gas at the outlet of such a bed increases the efficiency of heat recovery from it.

The reactor preferably does not include in its shell a heat exchanger other than that provided by the tubes in the catalyst bed. Thus the gas is brought to the tube inlet temperature preferably outside the reactor shell: this temperature is chosen so that the heat evolved in the synthesis reaction is taken up in raising the gas to the catalyst inlet temperature. The absence of such a heat exchanger increases the possible quantity of catalyst in a reactor shell of a given volume.

The tube supporting means preferably comprises a set of headers from which the tubes project upwardly through the bed. The tubes are preferably not rigidly linked together otherwise than by the headers but are kept in position by one or more planar linked-ring frameworks permeable to catalyst particles, slidingly applied to the tubes and secured against vertical movement. The resulting assembly is, apart from the upper ends of the tubes, immersed in a single body of catalyst particles; any part of the body beneath the headers constitutes the uncooled bed.

The means feeding the gas from the upper end of the tubes is conveniently a closed chamber above the surface of the catalyst.

In an alternative arrangement the tubes are Field tubes, each closed at its bottom and fed by way of an internal tube leading downwards from an upper set of headers or a chamber.

The reactor can be of the "hot-wall" or cartridge type: in the latter event the space between the cartridge and the shell can constitute the source of the supply of reactant gas to the tubes. Preferably this is effected by means of vertical headers each extending upwardly from the bottom of the cartridge and each feeding a plurality of cooling tubes. An alternative structure would use the Field tube arrangement, supplying gas through headers at the top of the cartridge.

According to a second aspect the invention provides a process of ammonia synthesis at a pressure under 120 bar abs which is carried out in a bed of promoted iron catalyst in heat exchange with a coolant flowing in a direction generally parallel to the direction of reactant flow in the catalyst bed.

The pressure is preferably over 30 bar abs. The heat exchange surface area provided is preferably under 20, especially in the range 3 to 15 $m^2$ per $m^3$ of catalyst. This is substantially less than was considered necessary in high pressure ammonia synthesis.

This aspect of the invention rests on the realisation that the heat evolved per unit volume per unit time is relatively small because of the relatively large catalyst volumes practicable at low pressures. As a result, the heat exchange can be provided by a small number of relatively large tubes; and thus the justification for abandoning the tube-cooled catalyst bed in the medium pressure processes no longer applies. Our process is also favoured by the lower catalyst outlet temperatures used in the new low pressure processes, specifically in the range of 350°–410° C., instead of 400°–480° C. for the old high-pressure or medium pressure processes. These are catalyst bed outlet temperatures; it is evident that the temperature in regions of the catalyst remote from heat exchange surfaces must be higher, but in the low pressure processes is unlikely to damage the catalyst even at considerable distances from such surfaces. Thus the reactor preferably used is clearly more than a low-pressure analogue of the old high pressure reactor.

Such an ammonia synthesis process is very conveniently carried out in a reactor according to the invention but is not limited thereto; other possible reactor arrangements include horizontal gas flow or radial flow through a vertical annular-section bed.

The $H_2:N_2$ ratio can be approximately stoichiometric, that is, in the range 2.5 to 3 but is preferably in the range 1.0 to 2.5, especially 1.5 to 2.3, as disclosed in our co-pending European application No. 49967.

The invention provides also a methanol synthesis process over a copper-containing particulate catalyst in a reactor according to the invention.

The methanol synthesis is preferably at a pressure in the range 30–120 bar abs. and a temperature in the range 160°–300° C. The catalyst usually contains also zinc oxide and one or more further oxides, such as of chromium (and UK Pat. No. 1010871) or of a metal from Groups II–IV of the Periodic Table (our UK Pat. No. 1159035) or possibly for example manganese or vandium. For such a process the cooled catalyst bed has a heat transfer area in the range 5–20 $m^2$ per $m^3$ of catalyst.

The reactor is suitable also for the catalytic synthesis of dimethyl ether, of alcohols higher than methanol or of hydrocarbons, from carbon monoxide/hydrogen synthesis gases and for the zeolite-catalysed conversion of methanol and/or dimethyl ether to aromatic hydrocarbons, operated in isolation or in conjunction with catalytic synthesis thereof.

Preferred forms of the invention are shown in the accompanying drawings, in which.

Figure 1A:
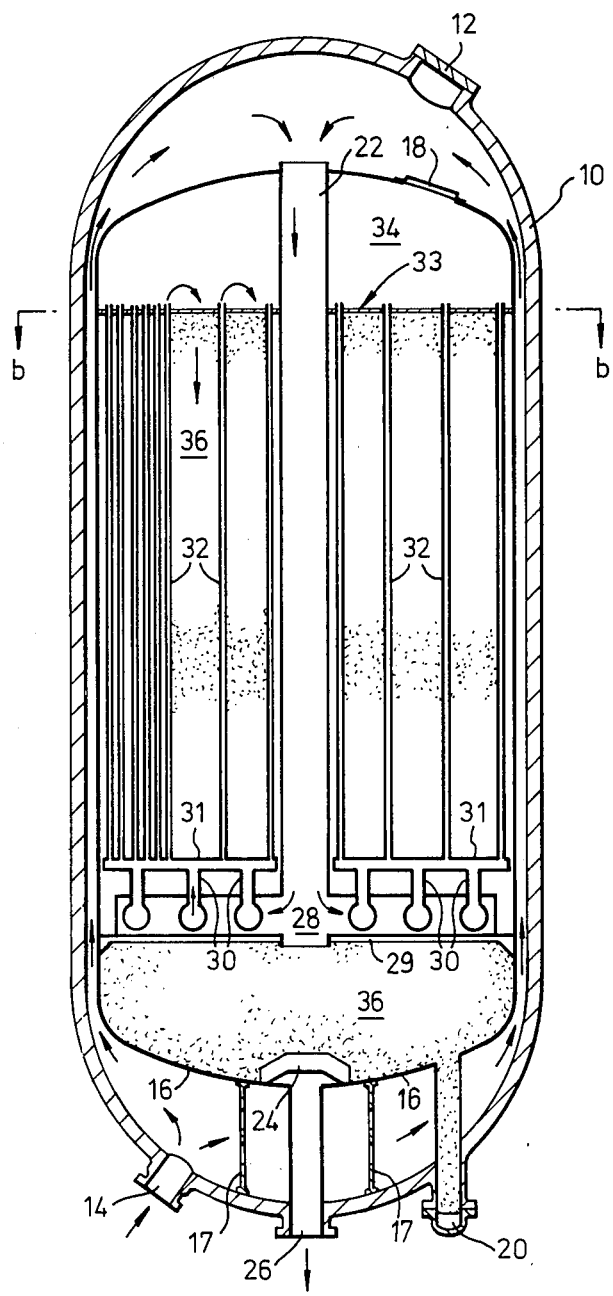
FIG. 1a is a sectional elevation of a reactor in which the process of ammonia synthesis or methanol synthesis can take place, and which itself is a further aspect of the invention.

In FIG. 1a reactor outer shell 10, constructed to withstand the pressure at which the synthesis is to operate, is formed with an upper manhole 12 for charging catalyst, a bottom gas inlet aperture 14 and two other bottom apertures to be described below. Within shell 10, supported by perforated ring-girder 17, is cartridge 16 which, since in operation gas at the same pressure will be outside and inside it, is made of relatively light-gauge metal. Cartidge 16 is formed with catalyst charging manholes 18 at its upper boundary and discharge port 20 at its lower boundary, port 20 passing through an aperture in shell 10. It is formed also with an aperture for gas inlet pipe 22, gas outlet sieve pipe 24 impervious to particulate catalyst, and gas outlet 26 leading through an aperture in shell 10. Gas inlet pipe 22 leads downwards to primary header 28, from which project secondary headers 30, from which in turn project tertiary headers 31 and thence cooling tubes 32 leading through promoted iron catalyst bed 36 into chamber 34. Header 28 as shown is one of a set of pipes arranged as the spokes of a wheel having its centre on the axis of pipe 22. These radiating spokes are supported by a set of transverse beams 29, of which one is shown, welded to the walls of cartridge 16. Beam 29 are disposed so as not to block the spaces between the pipes of header 28, and thus there is a single continuous body 36 of catalyst. Tubes 32 at or near their upper ends and also, if desired, at one or more intermediate levels, are kept at their required mutual separation by linked-ring framework 33, which like beams 29 and headers 28, 30 and 31, affords free passage of catalyst during charging or discharging the bed.

Figure 1B:
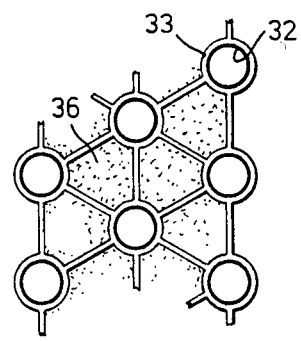
FIG. 1b is a section on line b—b in FIG. 1.

FIG. 1b shows the deposition of tubes 32 within linked-ring framework 33. Each tube 32 can be equipped with an internal core or turbulator or both, for all or part of its length, to increase gas velocity or turbulence and thus to improve heat transfer. Alternatively or in addition, tubes 32 can be finned.

In a hot-wall vessel the same internal constructional features would be present but cartridge 16 would be replaced by a pressure-resisting shell. External shell 10 is then, of course, not required and the reactants feed to the vessel is, after external preheating, direct to 22.

Figure 2:
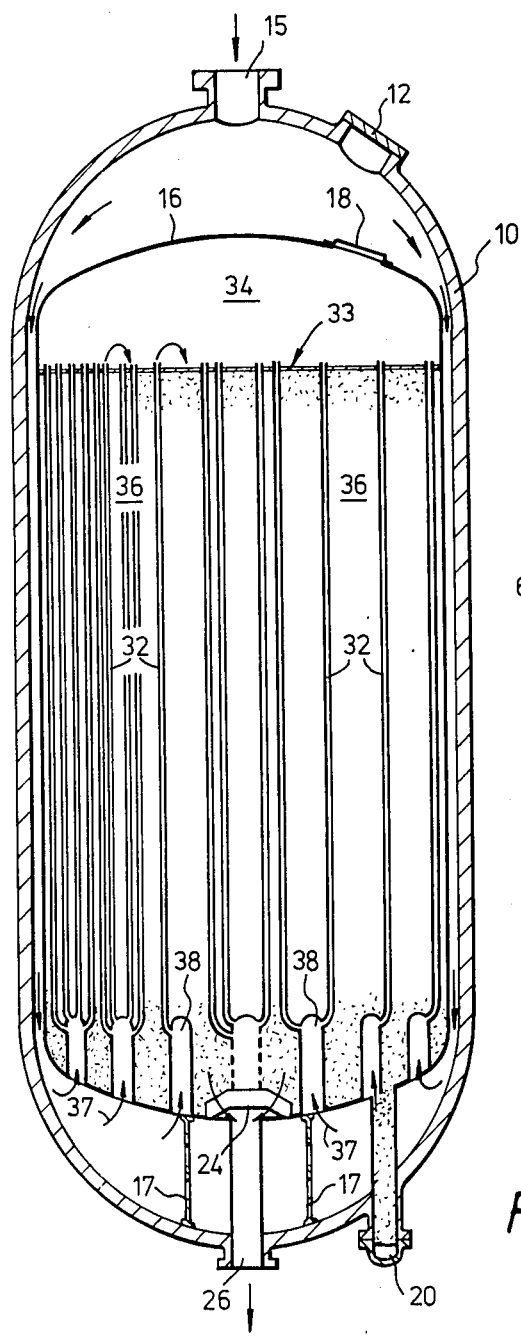
FIG. 2 is an alternative reactor according to the invention.

The reactor shown in FIG. 2 resembles that of FIG. 1 in its outer shell 10, manholes 12 and 18, cartridge 16, ring-girder 17, port 20, sieve plate 24, reacted gas outlet 26, tubes 32, chamber 34, catalyst 36 and ring framework 33. It differs, however, in the arrangements for supporting tubes 32 and introducing gas to them. The reactor gas inlet 15 is now at the top of shell 10. Cartridge 16 is formed on its underside with apertures 37: note that this region of FIG. 2 shows items 17, 20, 24, 26 and 37 which are not in the same plane of section. From each aperture 37 there extends upwards a vertical header 38, from which branch tubes 32. The lowermost part of catalyst bed 36 is not now fully adiabatic, since heat removal through vertical headers 38 can take place: if desired, these can be insulated, however.

The reactor of FIG. 2 could be modified to a hot-wall type by replacing cartridge 16 by the pressure-resisting shell and supplying internal vertical headers from an external lagged header.

Figure 3:
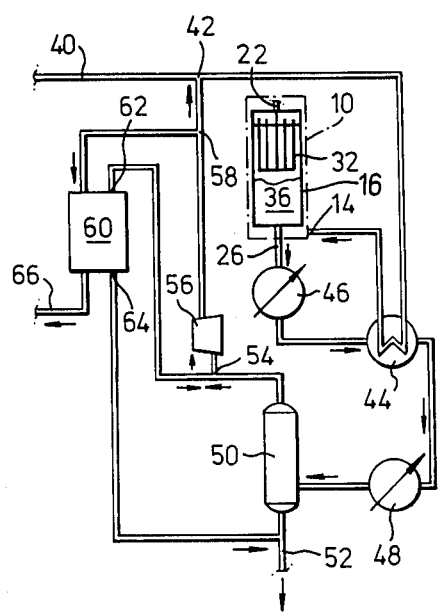
FIG. 3 is a flowsheet of a preferred process according to the invention.

In the flowsheet shown in FIG. 3, dry compressed fresh ammonia synthesis gas 40 from a generation section (typically comprising steam natural gas reforming, shift, $CO_2$-removal and residual carbon monoxide removal by methanation or selective oxidation) is mixed at 42 with recycle gas to be described and heated to eactor shell inlet temperature in secondary heat exchanger 44. It is then fed to reactor shell 10 at 14, heated further in the space between shell 10 and cartridge 16 and fed via gas inlet pipe 22 into tubes 32 in the upper portion of catalyst bed 36. In that upper portion synthesis take place and evolved heat is continuously removed by heat exchange with the gas inside tubes 32. In the lower portion of bed 36 further reaction takes place and the temperature is allowed to rise. The hot reacted gas is withdrawn by outlet 26 and cooled with external high-grade heat recovery (as boiler feed water, steam or steam superheat or more than one of these) in primary heat exchanger 46. It then passes to secondary heat exchanger 44 already mentioned, then to low grade heat recovery and final cooling (including moderate refrigeration) represented generally by 48. The temperature is now below the dewpoint of ammonia and the gas is passed catchpot 50 from which liquid product ammonia is run off at 52. Unreacted gas passes out overhead; at this stage it contains less hydrogen per nitrogen molecule than the gas fed to reactor 10, because ammonia formation uses three $H_2$ molecules per nitrogen molecule, but at 54 it receives a feed of hydrogen-rich gas to be described below. The mixed gas is fed to circulator 56, which increases its pressure by 10-20%, and is then divided at 58 into a synthesis recycle stream (which is fed to point 42) and a hydrogen recovery stream. This stream is fed to separation section 60. Here it is washed with water to remove ammonia, dried and resolved cryogenically or by absorption or selective diffusion into the hydrogen-rich stream fed to point 54 and a waste stream 66, which may have fuel value. The aqueous ammonia is distilled under pressure and the resulting anhydrous ammonia is fed out at 64 to the main product offtake 52.

For methanol synthesis the flowsheet shown in FIG. 3 can be used as a whole but is more commonly modified by omission of shell 10 and of item 10 and the connections to and from it, that is, by using a hot-wall reactor. Dry compressed fresh methanol synthesis gas 40 from a generation section (typically comprising steam gas reforming, water removal) is mixed at 42 with recycle gas to be described and heated to reactor inlet temperature in secondary heat exchanger 44. It is then fed via gas inlet pipe 22 into tubes 32 in the upper portion of catalyst bed 36. In that upper portion synthesis takes place and evolved heat is continuously removed by heat exchange with the gas inside tubes 32. In the lower portion of bed 36 further reaction takes place and the temperature is allowed to rise. The hot reacted gas is withdrawn by outlet 26 and cooled with external heat recovery (as hot pressurised water or medium pressure steam) in primary heat exchanger 46. It them passes to secondary heat exchanger 44 already mentioned, then to low grade heat recovery and final cooling represented generally by 48. The temperature is now below the dewpoint of methanol and the gas is passed to catchpot 50 from which liquid product aqueous methanol is run off at 52. Unreacted gas passes out overhead and is fed to circulator 56, which increases its pressure by 10-20%, providing the synthesis recycle stream fed to point 42. A purge stream is taken at 58 and is usually passed out to other uses, for example as a fuel or as hydrogenating gas. However, it can be fed to separation section 60. Here it is washed with water to remove methanol, dried and resolved cryogenically or by absorption or selective diffusion into a hydrogen-rich stream and a waste stream 66, which may have fuel value. The hydrogen-rich stream can be returned to the methanol synthesis at 54 if the synthesis gas composition requires it or can be passed out to other uses, especially ammonia synthesis. Methanol recovered in item 60 is passed to the main product offtake and thence to distillative purification (not shown).

In a typical ammonia synthesis (output 1000 metric tons per day) the temperatures, pressures, gas compositions and flow rates are shown in the Table 1. The heat transfer area is 12 $m^2$ per $m^3$ of catalyst using tubes of 37 mm outside diameter.

TABLE 1

| Position | Temp. °C. | Press. bar abs. | Gas composition % v/v | | | | | Flow rate kg mol h$^{-1}$ |
| --- | --- | --- | --- | --- | --- | --- | --- | --- |
| | | | $H_2$ | $CH_4$ | Ar | $N_2$ | $NH_3$ | |
| 22 inlet | 255 | 87.0 | 60.47 | 6.73 | 1.56 | 27.49 | 3.75 | 27737 |
| 32 outlet | 396 | 87.0 | 60.47 | 6.73 | 1.56 | 27.49 | 3.75 | 27737 |
| 36 at 29 | 360 | 86.0 | 54.438 | 7.183 | 1.665 | 25.973 | 10.74 | 25984 |
| 24 | 401.7 | 85.5 | 51.797 | 7.382 | 1.711 | 25.31 | 13.8 | 25289 |

In a typical methanol synthesis process (output 2525 metric tons of methanol 100% per day) the temperatures, pressures, gas compositions and flow rates are as shown in Table 2.

TABLE 2

| Position | Temp. °C. | Pr. bar abs | Gas compositon % v/v | | | | | | | Flow rate kg mol h$^{-1}$ |
| --- | --- | --- | --- | --- | --- | --- | --- | --- | --- | --- |
| | | | CO | $CO_2$ | $H_2$ | $CH_4$ | $N_2$ | $CH_3OH$ | $H_2O$ | |
| 22 inlet | 100 | 79 | 4.82 | 3.23 | 82.71 | 8.50 | 0.32 | 0.33 | 0.09 | 85547 |
| 32 outlet | 240 | | | | | | | | | |
| 36 at 29 | 265.9 | 79 | 2.35 | 2.20 | 79.97 | 9.21 | 0.35 | 4.52 | 1.40 | 78971 |
| 24 | 269.8 | 77 | 2.24 | 2.18 | 79.89 | 9.23 | 0.35 | 4.67 | 1.42 | 78754 |

In this process the heat transfer area using tubes of outside diameter 37 mm is 13 $m^2$ per $m^3$ of catalyst.

The catalyst volume in both processes is 10-15% less than would be required using a conventional quench reactor. The reactor volume is lower, since as much as 75-90% of the cartridge volume can contain catalyst. Since the catalyst can be very easily discharged and replaced, the reactor volume for ammonia synthesis can be made still smaller by designing for a shorter catalyst life than has been customary, for example 2-5 instead of 4-10 years.

I claim:

1. A reactor suitable for the catalytic synthesis of ammonia or methanol comprising:
   (i) an outer shell constructed to withstand a pressure in the range 30 to 120 bar absolute;
   (ii) inlet means to supply reactant gas to said shell;
   (iii) outlet means to permit removal of reacted gas from said shell;
   (iv) means defining a single, vertically oriented, catalyst bed region within said shell, containing a fixed bed of particulate catalyst and including means defining a space above an upper surface of said catalyst bed;
(v) a plurality of spaced-apart header pipes immersed in said bed of particulate catalyst;
(vi) means to feed reactant gas from said inlet means to said header pipes;
(vii) a plurality of vertically oriented heat exchange tubes having open upper ends and extending upwardly from said header pipes, said tubes being immersed in said bed of particulate catalyst for substantially their whole length but opening at the upper ends into the space above the upper surface of the catalyst bed, so that the catalyst continuously fills the spaces between the tubes and between the header pipes thereby defining a tube containing portion of the catalyst bed, and the catalyst also extending below said header pipes thereby defining a catalyst bed portion having no heat exchange tubes extending therethrough; and
(viii) means to feed reacted gas from the lower end of the catalyst bed region to said outlet means.

2. A reactor according to claim 1 in which the heat exchange tubes are kept in position by one or more planar linked-ring frameworks permeable to catalyst particles, slidably applied to the tubes and secured against vertical movement.

3. A reactor according to claim 1 intended for use in ammonia synthesis at a pressure in the range 30-120 bar abs., in which the heat exchange surface in the tube containing portion of the catalyst bed is in the range 3-15 $m^2$ per $m^3$ of catalyst in said tube containing portion of the catalyst bed.

4. A reactor according to claim 1 intended for use in methanol synthesis at a pressure in the range 30-120 bar abs, in which the heat exchange surface in the tube containing portion of the catalyst bed is in the range 5-20 $m^2$ per $m^3$ of catalyst in the tube containing portion of the catalyst bed.

5. A reactor according to claim 1 wherein the catalyst bed region comprises a cartridge within, and spaced from the walls of, the shell and the means for supply of reactant gas from the inlet means to the header pipes includes the space between the cartridge and the shell wall.

6. A reactor according to claim 1 wherein there is no heat exchange surface within the shell other than that provided by the tubes in the catalyst bed region.

* * * * *